United States Patent
Bosma et al.

(10) Patent No.: US 6,241,746 B1
(45) Date of Patent: Jun. 5, 2001

(54) VASCULAR FILTER CONVERTIBLE TO A STENT AND METHOD

(75) Inventors: Gjalt Bosma, Opeinde; Hendrik G. Breedveld, Groningen; Horace R. Davis, Amersfoort, all of (NL)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/342,876

(22) Filed: Jun. 29, 1999

Related U.S. Application Data
(60) Provisional application No. 60/090,968, filed on Jun. 29, 1998.

(51) Int. Cl.[7] ............................................. A61M 29/00
(52) U.S. Cl. ............................................. 606/200; 606/191
(58) Field of Search ................................. 606/200, 191, 606/198, 195; 623/1.12, 1.2, 1.32, 1.36, 1.15

(56) References Cited

U.S. PATENT DOCUMENTS

| | | |
|---|---|---|
| 4,793,348 | 12/1988 | Palmaz . |
| 4,873,978 * | 10/1989 | Ginsburg ............................ 606/200 |
| 5,108,418 | 4/1992 | Lefebvre . |
| 5,234,458 | 8/1993 | Metais . |
| 5,242,462 | 9/1993 | El-Nounou et al. . |
| 5,329,942 | 7/1994 | Gunther et al. . |
| 5,350,398 | 9/1994 | Pavenik et al. . |
| 5,549,626 * | 8/1996 | Miller et al. .......................... 606/191 |
| 5,709,704 | 1/1998 | Nott et al. . |
| 5,720,764 | 2/1998 | Naderlinger . |

FOREIGN PATENT DOCUMENTS

| | | |
|---|---|---|
| 40 30 998 A1 | 4/1991 | (DE) . |
| 195 09 464 C1 | 6/1996 | (DE) . |
| 98/02112 | 1/1998 | (WO) . |

* cited by examiner

Primary Examiner—Kevin Truong
(74) Attorney, Agent, or Firm—Michael W. Montgomery

(57) ABSTRACT

A vascular filter for temporary or permanent implantation within a body vessel to filter particulates or thrombus in the blood stream, is capable of being converted some time after initial implantation into a tubular stent. In this configuration, the stent tends to hold the vessel open without any significant filtering effect. The convertible filter/stent may have a tubular metal mesh structure. Also, the device may form one or more filter lattices when in the filter configuration.

5 Claims, 3 Drawing Sheets

VASCULAR FILTER CONVERTIBLE TO A STENT AND METHOD

This application claims the benefit of U.S. Provisional Application No. 60/090,968 filed Jun. 29, 1998 now expired.

BACKGROUND AND SUMMARY OF THE INVENTION

1. Technical Background

The present invention relates generally to medical devices, and more particularly to a vascular medical device.

2. Discussion

Vascular filters may be used for a variety of therapeutic applications, including implantable vena cava filters for capturing thrombus, or for distal protection during a vascular procedure.

Numerous different vascular filters are known of various types and designs. Prior filters are generally designed for either temporary use, such as may be provided on a catheter or provided with a mechanism for retrieving the filter, or for permanent implantation. Either a permanent or a temporary filter maybe preferred for a specific situation, given the specific therapeutic conditions and the properties of the filter.

The present invention relates to a filter system including a vascular filter that can be placed inside a body passage or cavity, such as a blood vessel, through a catheter consisting of a tubular basic body with a distal end, a proximal end and a catheter lumen extending in between the ends. The vascular filter can be received in a compressed state inside the catheter lumen, and the catheter is provided with an ejection device which can be used to eject the vascular filter from the distal end of the catheter.

Vascular filters of the type that are implanted in a patient's body vessel are often made of an elastic or so-called "memory" material. The vascular filter is positioned by using an ejection member to push the filter from the open distal tip of the catheter into the blood vessel.

Many prior vascular filters expand resiliently from the compressed state inside the catheter lumen to an enlarged or deployed state, when released or deployed at the desired site for treatment.

However, it is desirable to provide a filter capable of being implanted for a selectively variable duration. For example, a vascular filter according to the present invention might have a design such that the filter is deployed through a catheter, and then the filter may be transformed at a selected time later to provide an open "through lumen".

The present invention provides a novel vascular filter having a hybrid configuration, which is capable of being transformed to provide a through lumen at a time selected later.

Accordingly, it is desirable to provide a vascular filter capable of being implanted in an initial "filtering" configuration. The device may be monitored periodically for a time, until the physician decides to convert the implanted filter into a stent, for example. The filter is thus designed to selectively metamorphose into a second stent or graft configuration, providing a resilient tubular scaffold having and tending to maintain an open lumen through the body passageway.

Of course, the present invention relates broadly to vascular filters that are convertible into an open lumen device. The present invention may therefore be practiced in a multitude of different designs and variations which will occur to an average practitioner in the art.

These and various other objects, advantages and features of the invention will become apparent from the following description and claims, when considered in conjunction with the appended drawings.

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
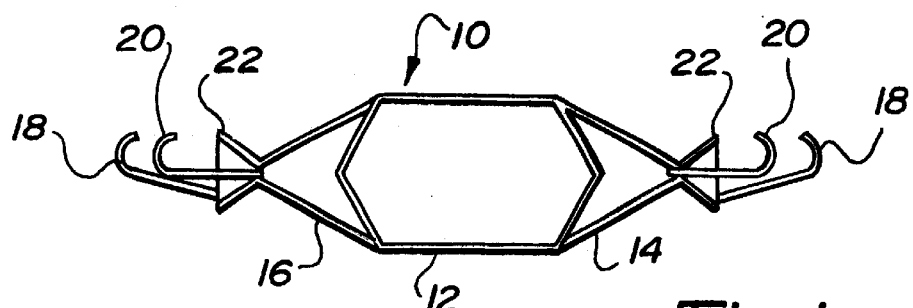
FIG. 1 is a diagrammatic side elevational view of a convertible vascular filter, arranged according to one embodiment of the principles of the present invention.
Figure 2:
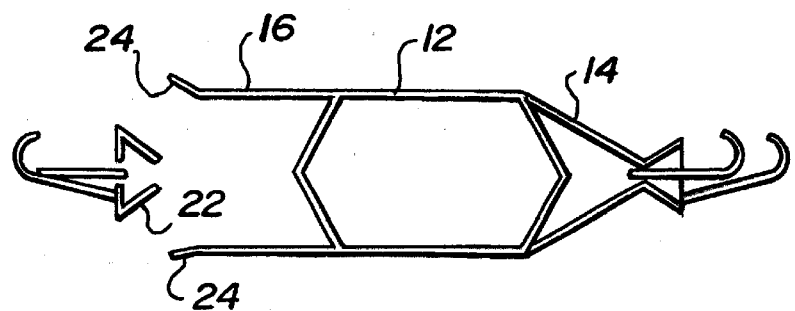
FIGS. 2 and 3 are diagrammatic side elevational views of the convertible vascular filter, showing operation of the device during transformation.
Figure 3:
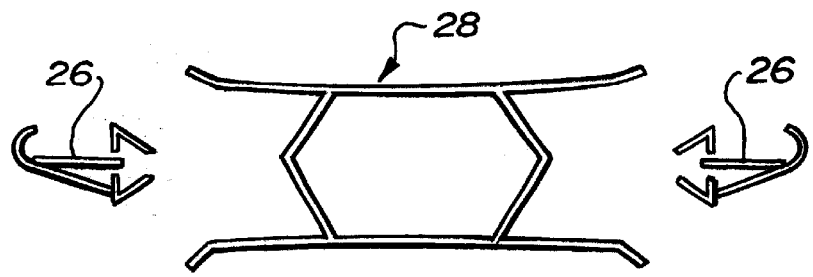

Referring to the drawings, in FIG. 1 a vascular filter 10 according to the present invention has been illustrated. According to the specific embodiment shown in FIGS 1–4, the filter 10 has several longitudinal ribs 12 supporting a first and second filter element or lattice 14 and 16. For the sake of drawing clarity, all of the ribs and the wires of filter elements have not been illustrated. Of course, there may be many filter elements or lattices, arranged in whatever preferred design is selected. In the arrangement shown in FIGS. 1–4, the filter elements 14 and 16 have a minimal number of converging wires.

One benefit of a design having more than one filter element coupled by longitudinal ribs is that the vascular filter 10 tends to deploy and align itself properly with the axis of the body passage or blood vessel.

In addition, the filter may be provided with a set of circumferential resilient supports, adapted to both hold the vascular filter in place, and also to ultimately hold open the body passage when the filter is converted into a stent.

As shown in FIG. 1, the filter elements 14 and 16 are held together by removable clamps 22. The clamps 22 are locked by pins 26, and both the pins 26 and clamps 22 have removal hooks 18 and 20 attached.

Before the filter is delivered and deployed in the patient's body, it is first loaded into a delivery catheter. In the distal tip of the catheter, at least one vascular filter is initially arranged in a compressed state. As an alternative, it is also possible that the filter is pushed along the entire length of the catheter from its proximal end to its distal end, after the catheter distal end has been advanced to the desired position. Preferably the filter is packed, in a compressed state, in transport packaging forming a covering. The vascular filter may be ejected from the distal tip of the catheter by a pushing wire and introduced into a blood vessel. Due to the release from the radially compressive force imposed by the catheter lumen at the distal tip of the catheter, the vascular filter will tend to expand resiliently to obtain an expanded shape. Liquid inside the blood vessel can pass through in an unimpeded fashion, but thrombus will tend to be intercepted by one of the two filter lattices.

An advantage of this configuration is that it provides two filter elements for intercepting thrombus moving inside a blood vessel, which may be more effective than one. In addition, due to the configuration of the ribs which extend along the internal wall of the blood vessel, no free ends are presented which might damage the internal wall of the blood vessel. The configuration of the vascular filter according to the embodiment illustrated is consequently designed so as to minimize any distress or damage to the blood vessel inside of which it has been arranged. As filter elements have been arranged on either side of the ribs and consequently a symmetrical shape has been obtained, there is no difference in the performance of the filter regarding the direction from which this vascular filter 10 has been placed inside the blood vessel.

As has been illustrated, the grid shape of each of the filters is such that each of the ribs is connected with a number of the components of these filters. Furthermore, each of the ribs is connected with both filters on either side. Due to this configuration, an added safety feature is that the filter has a fail-safe design.

In addition, tipping over or misalignment of either filter is less likely due to the more or less tubular shape into which the ribs have been arranged so that positioning of the vascular filter 10 inside the blood vessel can take place with unprecedented stability and reliability.

The vascular filter 10 is preferably made of a very resilient material, like nitinol. Following the ejection from the distal tip of the catheter, filter 10 can expand and will be pressed against the internal wall of the blood vessel.

Figure 4:
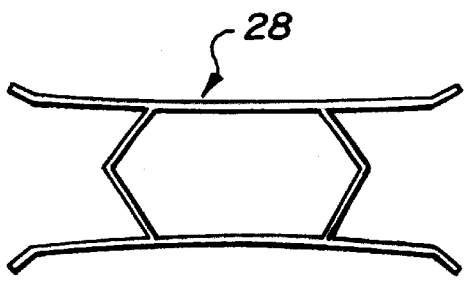
FIG. 4 is a diagrammatic side elevational view of the vascular filter of FIG. 1, after transformation into a stent.
Figure 4A:
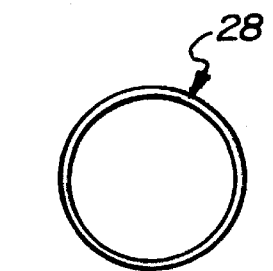
FIG. 4A is an axial longitudinal view of the stent of FIG. 4.

When the physician decides to transform the vascular filter into a stent, a catheter may be reinserted to a position near the filter. A guidewire with a hook can be used to pull the hook 20 attached to a locking pin 26. With the removal of the locking pin 26, the ends of the filter element collapse together, and the clamp 22 loses its purchase. The clamp 22 and locking pin 26 are then pulled by their attached hooks 18 and 20 out through the catheter, and the members forming filter elements 14 and 16 resiliently expand as in FIGS. 2–3. The resulting configuration is one of a resilient tubular stent 28 defining an open through lumen, as shown in FIGS. 4 and 4A.

The locking pin 26 and clamp22 at the other end of the filter may be accessed and removed by approaching the filter from the other vascular direction.

Another embodiment of the present invention is illustrated in FIGS. 5–10. The vascular filter 30 is shown having a "lobster pot" configuration including a number of longitudinal ribs 42, as well as transverse or circumferential support members.

Figure 5:
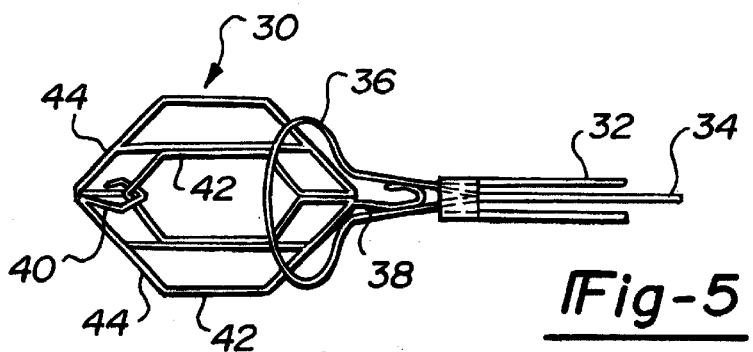
FIG. 5 shows a convertible vascular filter arranged according to the principles of the present invention in an initial filter configuration before being transformed into a stent configuration.

A pair of hooks 38 and 40 are provided at the proximal and distal ends for the filter. The hooks 38 and 40 may of course be formed as a shaped extension of one of the filter wires or ribs 42. As shown in FIG. 5, both hooks 38 and 40 preferably extend from a center region of a filter element 44 in a proximal direction. This feature offers the advantage of releasing both filter elements 44 into the stent configuration with a catheter approaching the filter from only one direction.

The wires of each filter lattice 44 are held together by closing wires 52.

Figure 6:
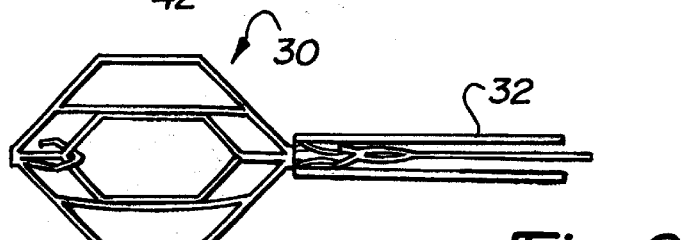
FIG. 6 shows the vascular filter of FIG. 5, after a catheter has snared a proximal end hook of the filter.

A catheter 32 and snare loop 34 may be used to convert the filter 30 into a stent configuration. After the snare 34 catches the proximal hook 38, it pulls the hook 38 and the closing wires 52 at the ends of the filter wires into the distal end of the catheter 32, as shown in FIG. 6. Inside the catheter distal end are a series of cutting members or knives 50, adapted to cut the closing wires 52 of the filter 30. When the closing wires 52 are severed, the filter wires resiliently expand to form the desired tubular stent configuration. Of course, the hooks 38 and 40 are specifically arranged to be flat against the body vessel wall in the stent configuration.

Figure 7:
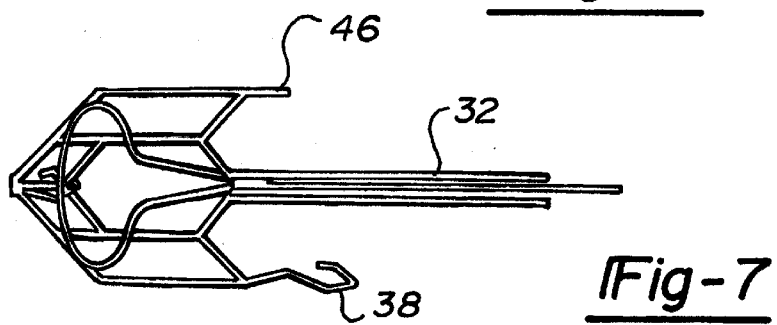
FIG. 7 shows the vascular filter of FIG. 6, after the proximal end of the filter has been opened, and illustrating the distal end hook being snared.
Figure 8:
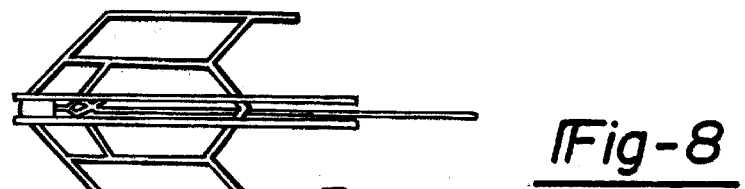
FIG. 8 shows the vascular filter of FIG. 7, after a catheter has snared a distal end hook of the filter.
Figure 9:
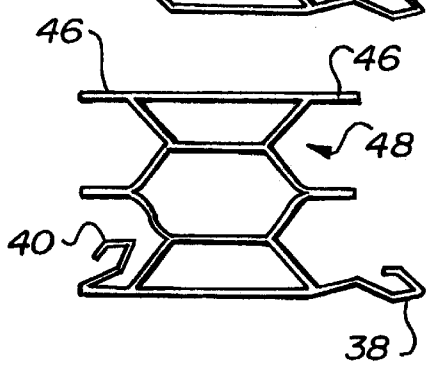
FIG. 9 shows the convertible vascular filter of FIGS. 5–8, after being transformed into a tubular stent.
Figure 10:
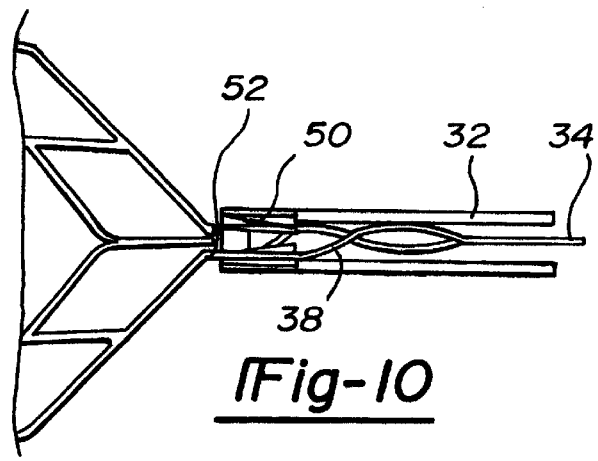
FIG. 10 is a partial view of the catheter and snare system of FIGS. 5–8 in greater detail.

As shown in FIGS. 7–8, the distal end of the filter is released in a similar manner, and the resulting stent is shown in FIG. 9.

Figure 12:
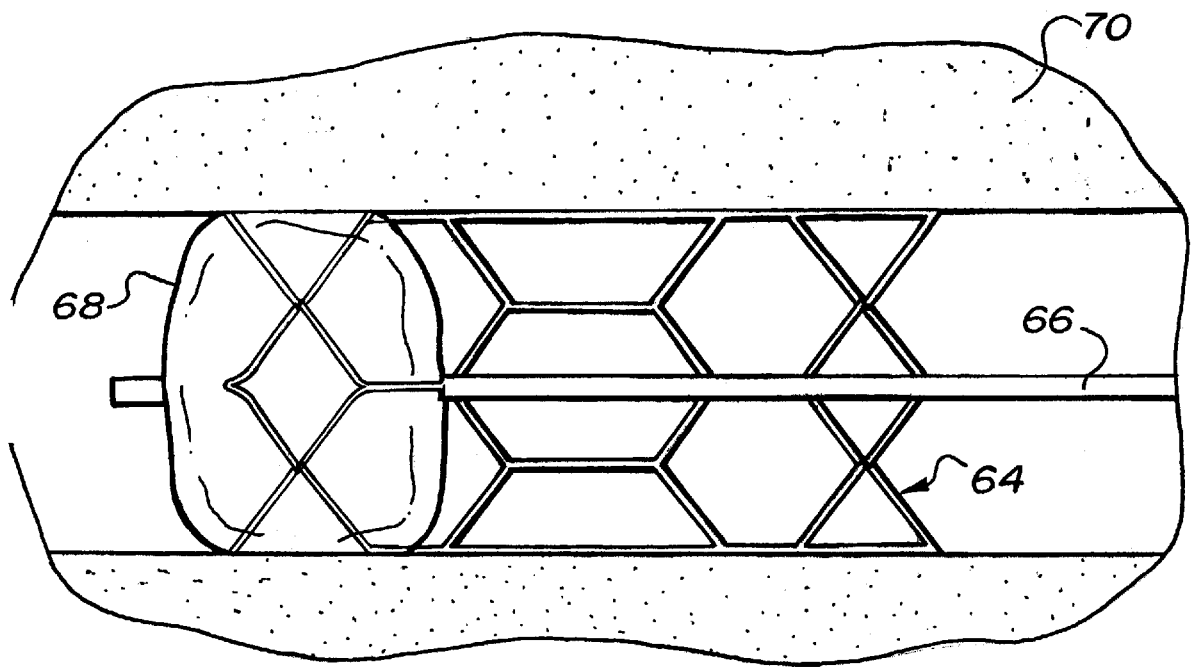
FIG. 12 is a side elevational view of the vascular filter of FIG. 11, showing the filter being converted into a stent by inflating the end portions with a balloon catheter.
Figure 11:
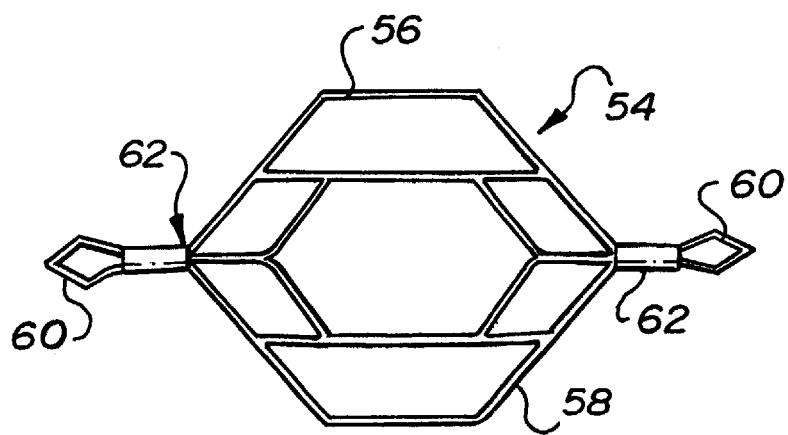
FIG. 11 is a side elevational view of yet another embodiment of a convertible vascular filter, arranged according to the present invention.

Yet another embodiment of the present invention is shown in FIGS. 11–12. The vascular filter is a hybrid combination of a central resilient "self-expanding"portion 54 flanked by two "balloon expandable" portions 62.

The self-expanding central portion 54 always tends to resiliently expand, being made for example of nitinol, while the balloon expandable portions 62 tend to remain compressed until forcibly expanded, being made for example of stainless steel.

The self-expanding filter portion 54 is permanently affixed to the balloon expandable stent portions 62, which may be affixed to a pair of hooks or loops 60 for maneuvering the device. The components may be affixed for example by welding.

When the physician decides to convert the filter into a stent, the balloon expandable stent or collar portions 62 are forcibly expanded such as by a balloon 66 of a balloon catheter 68, as shown in FIG. 12.

One advantage of the embodiment of a vascular filter according to the present invention is that the loop 60 may be used to later remove the vascular filter. Loops 60 can thus serve as a target for a hook-shaped extraction element, in order to remove the vascular filter. The hook-shaped extraction body (not shown) may engage the loop, and pull the entire vascular filter back into a catheter enveloping the extraction element.

After reading the above, many possible embodiments of a vascular filter that is convertible into a medical device forming an open lumen, other embodiments, and features will occur to one of ordinary skill in the field. All of these are to be considered as falling within the scope of the attached claims. It is for instance possible to use a vascular filter which has a different shape than the one described above. It is also possible to use a more conventional single vascular filter without the double filter feature. The vascular filter also does not need to comprise ribs extending in an axial direction in relation to the blood vessel.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claim is:

1. A vascular filter capable of being converted into a tubular stent for use in a desired site in a body passage for therapeutic treatment of a patient, comprising:

at least one filter element having a compressed shape and expanded shape, the filter element tending to resiliently expand from the compressed shape to the expanded shape, such that when the filter element in the expanded shape is positioned at the desired site and immersed in a body fluid flowing past the desired site, the filter element is adapted to filter the body fluid;

at least one releasable closing element affixed to the filter element and holding the filter element together in a filter configuration, such that the closing element, when released, causes the filter element to open and form a tubular stent defining an open lumen.

2. The vascular filter as set forth in claim 1, wherein the filter element is integrated and unitary.

3. The vascular filter as set forth in claim 1, wherein at least a portion of the filter is formed of nitinol.

4. The vascular filter as set forth in claim 1, wherein the closing element is removable from a remainder of the filter.

5. The vascular filter as set forth in claim 1, wherein the filter element is formed by a plurality of filter wires, each having an end, wherein the closing element is formed as one or more closing wires initially holding together the filter wire ends.

* * * * *